(12) United States Patent
Takayanagi et al.

(10) Patent No.: US 12,076,585 B2
(45) Date of Patent: Sep. 3, 2024

(54) TREATMENT PLANNING SYSTEM, TREATMENT PLANNING GENERATION METHOD, AND RECORDING MEDIUM

(71) Applicant: Hitachi, Ltd., Tokyo (JP)

(72) Inventors: Taisuke Takayanagi, Tokyo (JP); Takahiro Yamada, Tokyo (JP); Yusuke Fujii, Tokyo (JP); Toru Umekawa, Tokyo (JP); Hiroki Shirato, Hokkaido (JP); Shinichi Shimizu, Hokkaido (JP); Taeko Matsuura, Hokkaido (JP); Naoki Miyamoto, Hokkaido (JP); Seishin Takao, Sapporo (JP); Yuichi Hirata, Hokkaido (JP); Sodai Tanaka, Hokkaido (JP)

(73) Assignee: HITACHI, LTD., Tokyo (JP)

( * ) Notice: Subject to any disclaimer, the term of this patent is extended or adjusted under 35 U.S.C. 154(b) by 164 days.

(21) Appl. No.: 17/546,505

(22) Filed: Dec. 9, 2021

(65) Prior Publication Data
US 2022/0314027 A1  Oct. 6, 2022

(30) Foreign Application Priority Data
Mar. 30, 2021  (JP) ................. 2021-057201

(51) Int. Cl.
*A61N 5/10* (2006.01)
(52) U.S. Cl.
CPC ......... *A61N 5/1031* (2013.01); *A61N 5/1043* (2013.01); *A61N 5/1048* (2013.01);
(Continued)

(58) Field of Classification Search
CPC ........ A61N 5/10; A61N 5/103; A61N 5/1031; A61N 5/1037; A61N 5/1042;
(Continued)

(56) References Cited

U.S. PATENT DOCUMENTS 6,774,383 B2 * 8/2004 Norimine ............. A61N 5/1048
378/65
8,581,218 B2 * 11/2013 Fujimoto ............. A61N 5/1043
250/397
(Continued)

FOREIGN PATENT DOCUMENTS

| JP | 2016-532530 A | 10/2016 |
| JP | 2017-522097 A | 8/2017 |
| WO | 2018/116354 A1 | 6/2018 |

OTHER PUBLICATIONS

An English translation of JP2016-532530A by Patent Translate. (Year: 2024).*

(Continued)

Primary Examiner — Allen C. Ho
(74) Attorney, Agent, or Firm — MATTINGLY & MALUR, PC

(57) ABSTRACT

A treatment planning system that generates treatment planning for irradiating a target with a particle beam, includes an arithmetic processing device that sets at least two or more irradiation patterns for one treatment planning, calculates a plurality of predicted dose distributions for each irradiation pattern based on a target dose set for each region for at least one region including a region of the target, and calculates an index for evaluating validity of the irradiation pattern based on the plurality of predicted dose distributions.

11 Claims, 12 Drawing Sheets

(52) U.S. Cl.
CPC ............... *A61N 2005/1074* (2013.01); *A61N 2005/1087* (2013.01)

(58) Field of Classification Search
CPC .. A61N 5/1043; A61N 5/1048; A61N 5/1049; A61N 5/1064; A61N 5/1065; A61N 5/1067; A61N 5/1071; A61N 2005/1072; A61N 2005/1074; A61N 5/1077; A61N 5/1078; A61N 2005/1085; A61N 2005/1087; A61N 2005/1089; A61N 2005/1091; A61N 5/1044; A61N 5/1045; A61N 5/1047; A61N 5/1081; A61N 5/1082
USPC ....................................................... 378/64, 65
See application file for complete search history.

(56) References Cited

U.S. PATENT DOCUMENTS

| | | | | |
|---|---|---|---|---|
| 8,775,207 | B2* | 7/2014 | Abraham | G16H 20/40 378/65 |
| 8,822,958 | B2* | 9/2014 | Hirayama | G21K 5/00 250/492.1 |
| 8,916,841 | B2* | 12/2014 | Totake | A61N 5/1048 250/397 |
| 9,364,686 | B2* | 6/2016 | Hastenteufel | A61N 5/1031 |
| 9,393,443 | B2* | 7/2016 | Fujimoto | A61N 5/1037 |
| 9,409,039 | B2* | 8/2016 | Hartman | A61N 5/1031 |
| 9,630,024 | B2* | 4/2017 | Hirayama | A61N 5/1031 |
| 9,827,445 | B2* | 11/2017 | Cordero Marcos | G16H 20/40 |
| 9,860,969 | B2* | 1/2018 | Okazaki | H05H 13/04 |
| 10,046,177 | B2 | 8/2018 | Sjölund et al. | |
| 10,376,713 | B2* | 8/2019 | Takayanagi | A61N 5/1031 |
| 10,751,546 | B2* | 8/2020 | Takayanagi | A61N 5/1031 |
| 10,762,167 | B2* | 9/2020 | Hartman | A61N 5/103 |
| 11,160,994 | B2* | 11/2021 | Ono | A61N 5/1043 |
| 11,167,150 | B2* | 11/2021 | Löf | G16H 40/20 |
| 11,369,804 | B2* | 6/2022 | Soukup | G16H 20/40 |
| 11,402,523 | B2* | 8/2022 | Menichelli | G01T 1/2921 |
| 11,426,603 | B2* | 8/2022 | Kobashi | A61N 5/1037 |
| 11,679,274 | B2* | 6/2023 | Peltola | A61N 5/1031 378/65 |
| 11,724,126 | B2* | 8/2023 | Adelsheim | A61N 5/1081 600/1 |
| 11,850,445 | B2* | 12/2023 | Hibbard | G16H 50/20 |
| 11,904,185 | B2* | 2/2024 | Hirayama | A61N 5/1049 |
| 2016/0144198 | A1 | 5/2016 | Lof | |

OTHER PUBLICATIONS

Tsuguhide Takeshima, et al., "Local Radiation Therapy Inhibits Tumor Growth through the Generation of Tumor-Specific CTL: Its Potentiation by Combination with Th1 Cell Therapy", Cancer Research , 70 (7), Apr. 1, 2010, pp. 2697-2706.

Japanese Office Action received in corresponding Japanese Application No. 2021-057201 dated Jan. 9, 2024.

* cited by examiner

TREATMENT PLANNING SYSTEM, TREATMENT PLANNING GENERATION METHOD, AND RECORDING MEDIUM

CROSS-REFERENCE TO RELATED APPLICATION

The present application claims priority from Japanese application JP 2021-057201, filed on Mar. 30, 2021, the contents of which is hereby incorporated by reference into this application.

BACKGROUND OF THE INVENTION

1. Field of the Invention

The present invention relates to a treatment planning system, a treatment planning generation method, and a computer program.

2. Description of the Related Art

A radiotherapy planning system numerically calculates a dose distribution in a patient's body based on information in the patient's body obtained from a CT image or the like. An operator determines an irradiation pattern such as an irradiation angle, energy, and an intensity distribution of the radiation in the lateral direction while referring to the obtained calculation result. Such a procedure is referred to as a treatment planning.

The general procedure for treatment planning is described below. The operator first inputs a target region to be irradiated with radiation on a CT image. There may be a plurality of target regions at distant locations. In most cases, a region group of organs at risk (OAR) to be avoided from being irradiated with radiation as much as possible is similarly input.

Next, the operator sets a target irradiation dose based on clinical knowledge for each input region. For example, a dose of 60 Gy is given to 95% or more of the volume of the target. For the OAR, for example, a restriction (dose constraint) such that a dose of 30 Gy or more should not be given to 60% or more of the volume is set. When there are a plurality of targets, the target dose may be different for each target. The dose constraint may be different for each OAR as well.

Subsequently, the operator obtains the most appropriate irradiation pattern satisfying the set target dose and dose constraint by optimization. The appropriate irradiation pattern specifically gives the maximum dose to the target within a range in which the OAR is not damaged. In the treatment planning system, an objective function that quantifies a deviation between the dose distribution calculated based on the irradiation pattern and the target dose/dose constraint may be used for optimization of the irradiation pattern. As an algorithm for minimizing the objective function, a quasi☐Newton method or the like is used.

In general, the dose application to the target and the dose reduction to the OAR are in a trade-off relationship, and the objective function of the OAR deteriorates as the objective function of the target improves. The operator adjusts parameters related to the optimization of the irradiation pattern, specifically, the weight of each objective function, and repeatedly operates the treatment planning system to determine the irradiation pattern determined to be clinically most appropriate.

As an index for determining whether the irradiation pattern obtained as a result of such a treatment planning is good or bad, there are a tumor control probability (TPC) and a normal tissue complication probability (NTCP). The invention is disclosed in which TCP and NTCP are calculated based on a dose distribution calculated based on an irradiation pattern and a biological model registered in advance in a treatment planning system, and are presented to an operator (for example, refer to JP 2017-522097 T). When the TCP and the NTCP do not reach the target values, it is necessary to correct the irradiation dose to the target and the number of times of divided irradiation (details will be described later), further adjust the dose constraint on the OAR and the optimization parameters (weights of the respective objective functions), and perform the optimization of the repeated irradiation pattern.

The divided irradiation described above will be described below. In the radiotherapy, in order to suppress NTCP of the OAR, divided irradiation is performed in which the daily irradiation dose to the target is suppressed to about 2 Gy and the treatment is performed over 20 to 30 days. However, in a case where the target is separated from the OAR, the dose delivery to the target has little impact on the NTCP of the OAR, and thus the daily irradiation dose can be increased and the number of times of division, or treatment days, can be reduced.

In recent years, in radiotherapy, the action of immunity associated with radiation irradiation has attracted attention. It has been known that when some cancer cells are killed by irradiation, a specific antigen is released from the killed cancer cells. When the immune cell recognizes a cancer antigen, the cancer cell is determined as a foreign substance, and attack on the remaining cancer cell is started. On the other hand, it has been known that when a lymph node is irradiated with radiation, immune cells are damaged by the radiation, and therefore, attack on cancer cells is weakened (refer to Takeshima. T, et al., "Local radiotherapy Inhibits Tumor Growth through the Generation of Tumor-Specific CTL: Its Potentiation by Combination with Th1 Cell Therapy" Cancer Res; 70 (7) Apr. 1, 2010).

SUMMARY OF THE INVENTION

In general, there is one irradiation pattern for one treatment planning, and the daily irradiation pattern and irradiation dose are the same. Therefore, for example, in a case where there are a plurality of targets having different distances from the OAR, the target existing at a distance close to the OAR becomes a bottleneck, and the number of times of division cannot be reduced for the target far away from the OAR.

For such a problem, it is considered effective to prepare a plurality of irradiation patterns for one treatment planning. For example, for a target distant from the OAR, the daily irradiation dose is increased and the treatment is completed in a short period of time. Thereafter, the irradiation pattern is changed, the daily irradiation dose is suppressed for a target adjacent to the OAR, and the treatment is performed for 20 to 30 days as before.

However, even if the total irradiation dose and the number of irradiation days can be set for each target region and the number of required irradiation patterns can be derived, there is no means for determining whether the irradiation pattern group clinically provides the maximum therapeutic effect. Even if some numerical index indicating the clinical effect is obtained, optimization of the entire irradiation pattern and dose calculation are essential to calculate the index. There has been a problem that it takes a huge amount of time to plan the treatment planning.

The present invention has been made in view of the above problems, and an object of the present invention is to provide a treatment planning system capable of planning treatment planning based on an index for evaluating the validity of an irradiation pattern in a short time in the treatment planning including a plurality of irradiation patterns, a treatment planning generation method, and a computer program.

In order to solve the above problems, according to one aspect of the present invention, a treatment planning system that generates treatment planning for irradiating a target with a particle beam, includes a control system that sets at least two or more irradiation patterns for one treatment planning, calculates a plurality of predicted dose distributions for each irradiation pattern based on a target dose set for each region for at least one region including a region of the target, and calculates an index for evaluating validity of the irradiation pattern based on the plurality of predicted dose distributions.

According to the present invention, in treatment planning including a plurality of irradiation patterns, treatment planning based on an index for evaluating the validity of the irradiation pattern can be planned in a short time.

DESCRIPTION OF THE PREFERRED EMBODIMENTS

Figure 1:
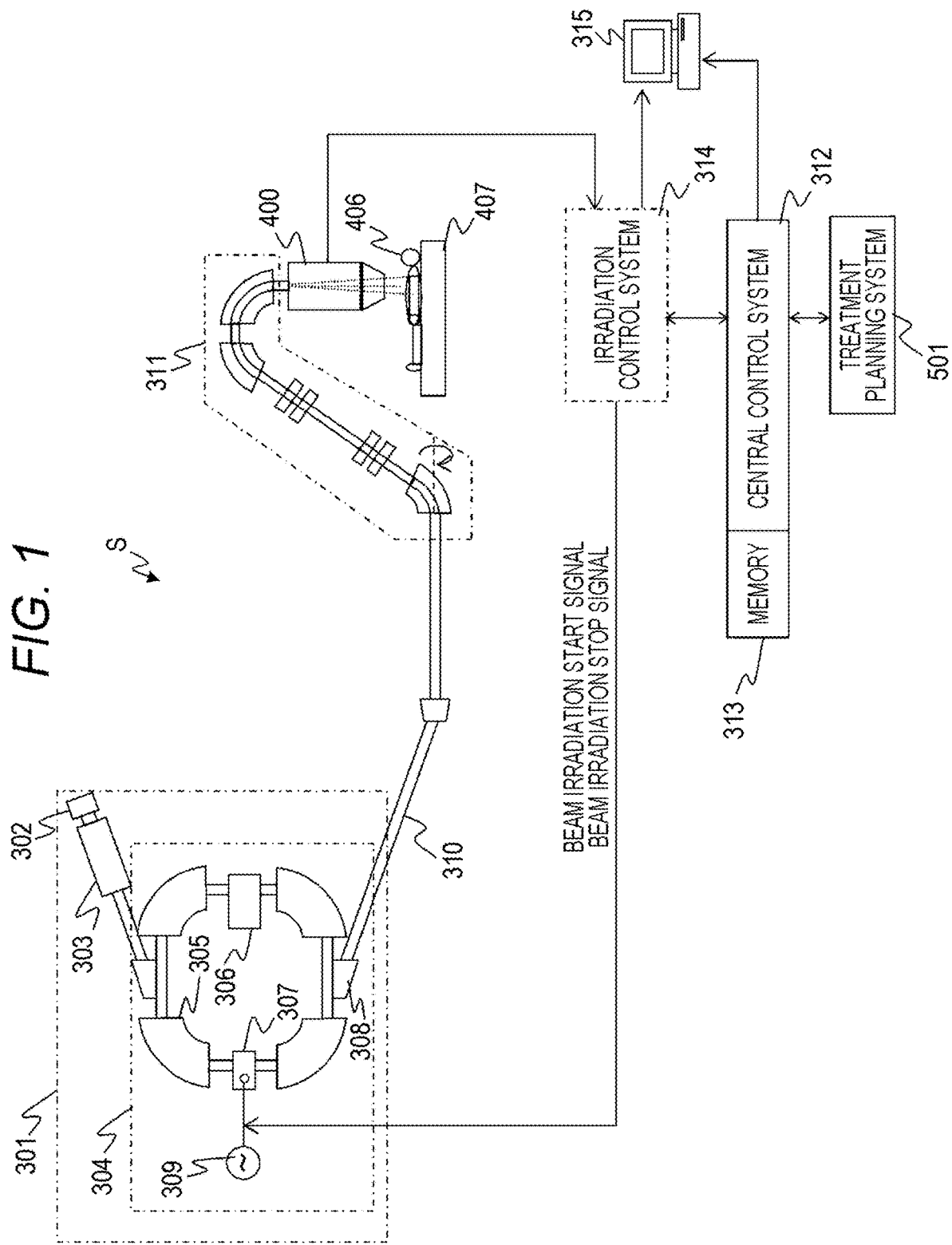
FIG. 1 is a schematic configuration diagram illustrating a particle therapy system including a treatment planning system according to a first embodiment.

Hereinafter, embodiments of the present invention will be described with reference to the drawings. The following description and drawings are examples for describing the present invention, and are omitted and simplified as appropriate for the sake of clarity of description. The present invention can be carried out in various other forms. Unless otherwise specified, each component may be singular or plural.

Note that, in the drawings for describing the embodiments, portions having the same functions are denoted by the same reference numerals, and repeated description thereof will be omitted.

Positions, sizes, shapes, ranges, and the like of the components illustrated in the drawings may not represent actual positions, sizes, shapes, ranges, and the like in order to facilitate understanding of the invention. Therefore, the present invention is not necessarily limited to the position, size, shape, range, and the like disclosed in the drawings.

In a case where there is a plurality of components having the same or similar functions, the same reference numerals may be attached with different subscripts for description. However, in a case where it is not necessary to distinguish the plurality of components, the description may be omitted.

First Embodiment

A radiotherapy planning system (hereinafter, simply referred to as a "treatment planning system") 501 according to first embodiment will be described with reference to FIGS. 1 to 8. In the present embodiment, a treatment planning system that plans treatment planning of proton beam therapy by a scanning irradiation method, which is a type of radiotherapy, will be described. However, the present invention is also applicable to a treatment planning system that plans treatment planning of proton beam therapy by a scattering irradiation method or heavy particle therapy using a carbon ion beam or the like. The present invention is also applicable to a treatment planning system for X-ray therapy.

FIG. 1 is a schematic configuration diagram illustrating a particle therapy system to which a treatment planning system according to an embodiment is applied.

In FIG. 1, a particle therapy system S according to the embodiment includes an ion beam generator 301, a high energy beam transport 310, a rotary irradiator 311, a central control system 312, a memory 313, an irradiation control system 314, a display device 315, an irradiation nozzle (irradiation device) 400, a bed 407, and a treatment planning system 501.

The ion beam generator 301 includes an ion source 302, a preaccelerator 303, and a particle beam acceleration system 304. In the present embodiment, a synchrotron type particle beam acceleration system is assumed as the particle beam acceleration system 304; however, any other particle beam acceleration system such as a cyclotron may be used as the particle beam acceleration system 304. As illustrated in FIG. 1, the synchrotron type particle beam acceleration system 304 includes a bending magnet 305, an acceleration system 306, a radiofrequency acceleration system 307 for extraction, an extraction deflector 308, and a quadrupole magnet (not shown) on a closed orbit thereof.

With reference to FIG. 1, the progress until the particle beam is generated from the ion beam generator 301 using the synchrotron type particle beam acceleration system 304 and extracted toward a patient 406 will be described.

The particles supplied from the ion source 302 are accelerated by the preaccelerator 303 and sent to a synchrotron which is the particle beam acceleration system 304. The acceleration system 306 is installed in the synchrotron, and a high frequency is applied to a high frequency accelerating cavity (not shown) provided in the acceleration system 306 in synchronization with a period in which a particle beam circulating in the synchrotron passes through the acceleration system 306 to accelerate the particle beam. In this way, the particle beam is accelerated until a predetermined energy is reached.

After the particle beam is accelerated to a predetermined energy (for example, 70 to 250 MeV), when an extraction start signal is output from the central control system 312 via the irradiation control system 314, high frequency power from a radiofrequency power supply 309 is applied to the particle beam circling in the synchrotron by an extraction radiofrequency electrode installed in the radiofrequency acceleration system 307, and the particle beam is extracted from the synchrotron.

The high energy beam transport 310 connects the synchrotron and the irradiation nozzle 400. The particle beam taken from the synchrotron is guided to the irradiation nozzle 400 installed in the rotary irradiator 311 via the high energy beam transport 310. The rotary irradiator 311 is for irradiating the beam from an optional direction of the patient 406, and can rotate in any direction around the bed 407 on which the patient 406 is installed by rotating the irradiator 311.

The irradiation nozzle 400 is a device that shapes the shape of the particle beam that finally irradiates the patient 406, and a structure thereof varies depending on an irradiation method. The scattering method and the scanning method are representative irradiation methods, and the particle therapy system S of the present embodiment is directed to the scanning method. In the scanning method, the target is irradiated with the thin beam transported from the high energy beam transport 310 as it is and three-dimensionally scanned, so that a high dose region can be finally formed only in the target.

Figure 2:
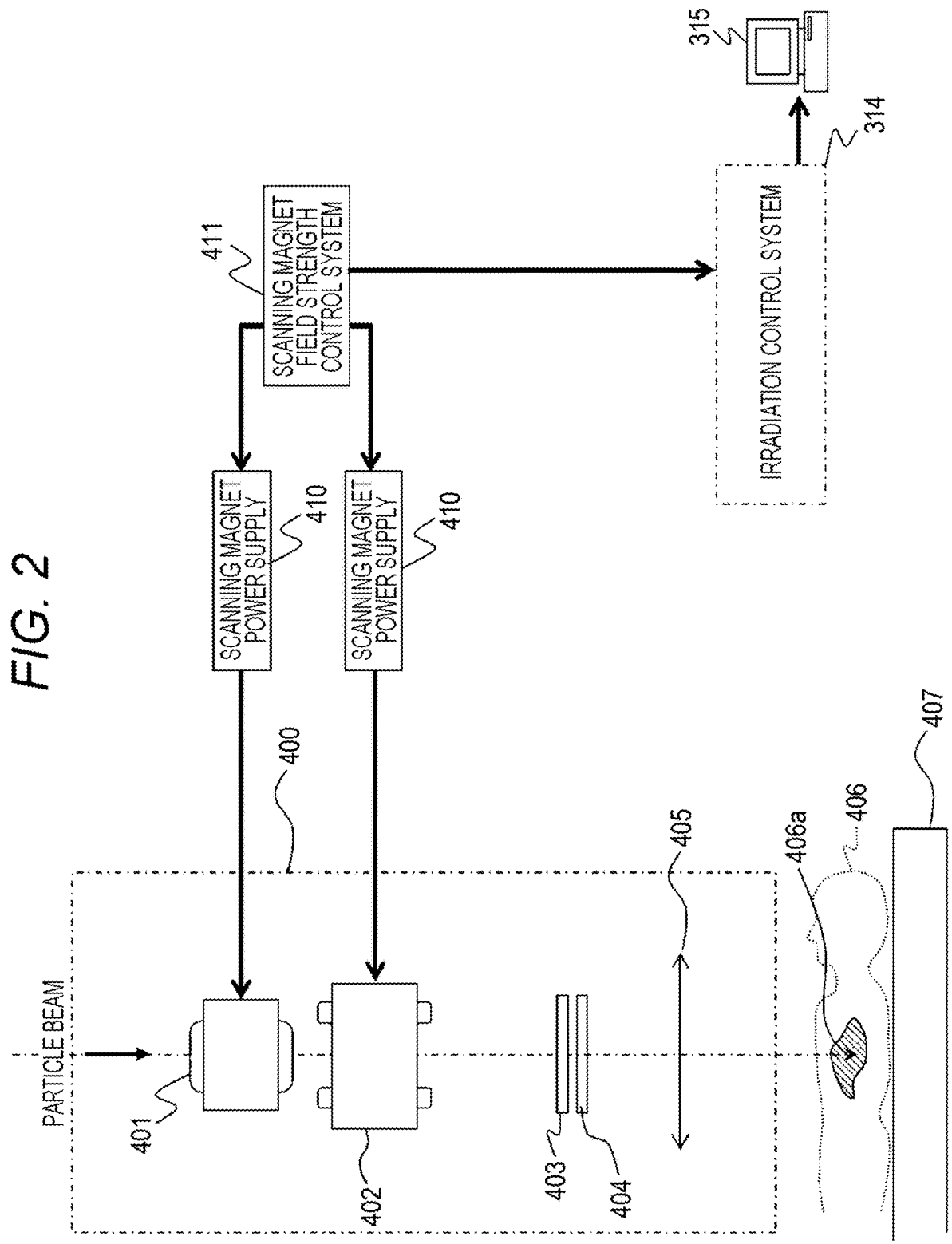
FIG. 2 is a diagram illustrating a configuration of an irradiation nozzle used in the particle therapy system according to the first embodiment.

FIG. 2 is a diagram illustrating a configuration of the irradiation nozzle 400 used in the particle therapy system S according to the embodiment. The irradiation nozzle 400 illustrated in FIG. 2 is compatible with a spot scanning method.

A role and a function of each device in the irradiation nozzle 400 will be briefly described with reference to FIG. 2. The irradiation nozzle 400 includes two scanning magnets 401 and 402, a dose monitor 403, and a beam position monitor 404 from the upstream side. The dose monitor 403 measures the amount of the particle beam that has passed through the monitor. On the other hand, the beam position monitor 404 can measure the position through which the particle beam has passed. Based on the information from the monitors 403 and 404, the irradiation control system 314 can manage that the planned position is irradiated with the planned amount of beam.

The thin particle beam transported from the ion beam generator 301 via the high energy beam transport 310 is deflected in a traveling direction thereof by the scanning magnets 401 and 402. These scanning magnets 401 and 402 are provided so that lines of magnetic force are generated in a direction perpendicular to the beam traveling direction. For example, in FIG. 2, the scanning magnet 401 deflects the beam in a direction of the scanning direction 405, and the scanning magnet 402 deflects the beam in a direction perpendicular thereto. By using the two magnets 401 and 402, the beam can be moved to an optional position in a plane perpendicular to the beam traveling direction, and a target 406a can be irradiated with the beam.

The irradiation control system 314 controls the amount of current flowing through the scanning magnets 401 and 402 via a scanning magnet field strength control system 411. The current is supplied from a scanning magnet power supply 410 to the scanning magnets 401 and 402, and a magnetic field corresponding to the amount of current is excited, so that the deflection amount of the beam can be freely set. The relationship between the deflection amount of the particle beam and the current amount is held in advance as a table in the memory 313 in the central control system 312, and the relationship is referred to.

Here, in the spot scanning method, points (spots) are three-dimensionally arranged inside and around a target region to be irradiated with radiation in a patient body, particularly a tumor or the like, and each spot is irradiated with a small-diameter beam. A prescribed irradiation dose is determined for each spot, and when a certain spot is irradiated with the prescription dose, the beam is deflected to the next spot to be irradiated, and the beam is irradiated again. By applying the prescription dose to all the spots, a uniform dose distribution is formed in the target region. Scanning irradiation includes a discrete method and a raster method. In the discrete method, the beam is temporarily stopped when the spot is switched. The raster method is a method in which the beam is not stopped even during the movement of the irradiation position.

In the following examples, the raster scanning method will be described, but the present embodiment can also be applied to the discrete scanning method.

Figure 3:
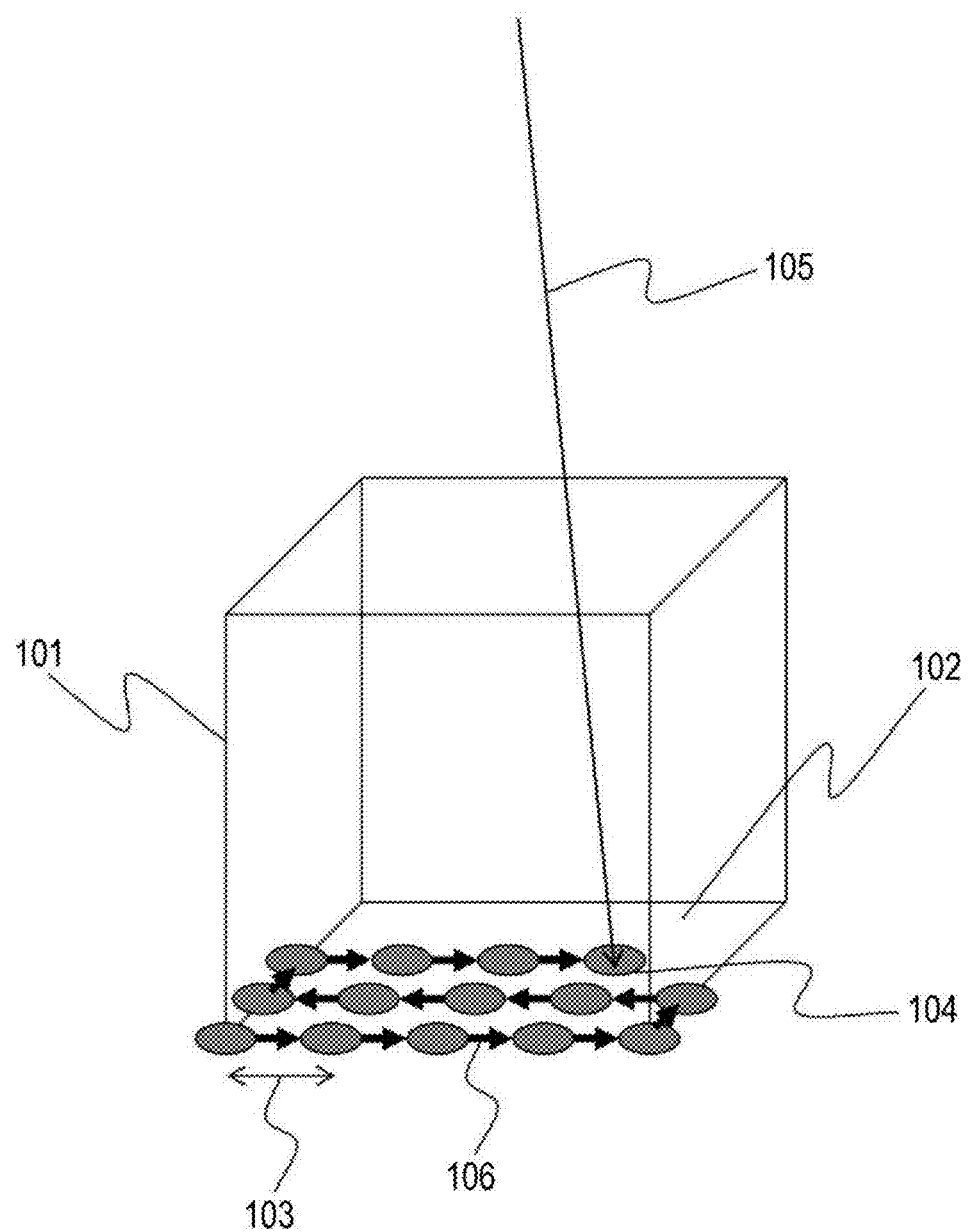
FIG. 3 is a perspective view illustrating a setting example of an irradiation position in a raster scanning method.

FIG. 3 is a perspective view illustrating a setting example of an irradiation position in a raster scanning method. FIG. 3 illustrates an example in which a cubic target 101 is irradiated.

In FIG. 3, the particle beam stops at a certain position in the traveling direction, and most of the energy is applied to the stop position. Therefore, the energy is adjusted so that the depth at which the particle beam stops is within the target region.

In the example of FIG. 3, a particle beam having energy that stops near a plane 102 irradiated with the same energy is selected. On the plane 102, irradiation spots 104 set as irradiation positions are arranged at a spot interval 103. When one irradiation spot 104 is irradiated with a predetermined amount of particle beam, the particle beam moves to the next irradiation spot 104, and the irradiation spot 104 at the moving destination is irradiated with the particle beam. A scanning path 106 of the particle beam can be set to, for example, a zigzag path. At this time, after the particle beam moves along an x-axis from an end to an end of the plane 102, the particle beam moves along a y-axis by the spot interval 103, and from there, the particle beam can repeatedly move along the x-axis from the end to the end of the plane 102.

The dose distribution of each irradiation spot 104 can be given by a Gaussian distribution. At this time, a spot interval 803 can be set such that the dose distribution of the entire plane 102 is flattened by overlapping of the Gaussian distributions of the respective irradiation spots 104.

The irradiation dose irradiated during the movement of the particle beam is also measured, and when the sum of the irradiation dose of the moving particle beam and the irradiation dose of the particle beam irradiated in a state of being stopped at the next irradiation spot 104 reaches a specified amount, the irradiation spot is further moved to the next irradiation spot 104. The irradiation spot 104 is irradiated with a particle beam passing through a trajectory 105 for irradiating the irradiation spot 104. When the irradiation spots 104 having the same energy arranged in the target 101 are sequentially irradiated, the depth at which the particle beam is stopped in the target 101 is changed in order to irradiate other depth positions in the target 101.

In order to change the depth at which the beam stops, the energy of the particle beam with which the target 101 is irradiated is changed. One way to change the energy is to change the setting of the particle beam acceleration system 304, that is, the synchrotron in this embodiment. The particles are accelerated to the energy set in the synchrotron, but the energy injected on the target 101 can be changed by changing the set value.

In this case, since the energy taken from the synchrotron changes, the energy when passing through the high energy beam transport 310 also changes, and it is also necessary to change the setting of the high energy beam transport 310. In the case of a synchrotron, it takes about 1 second to change the energy.

Figure 4:
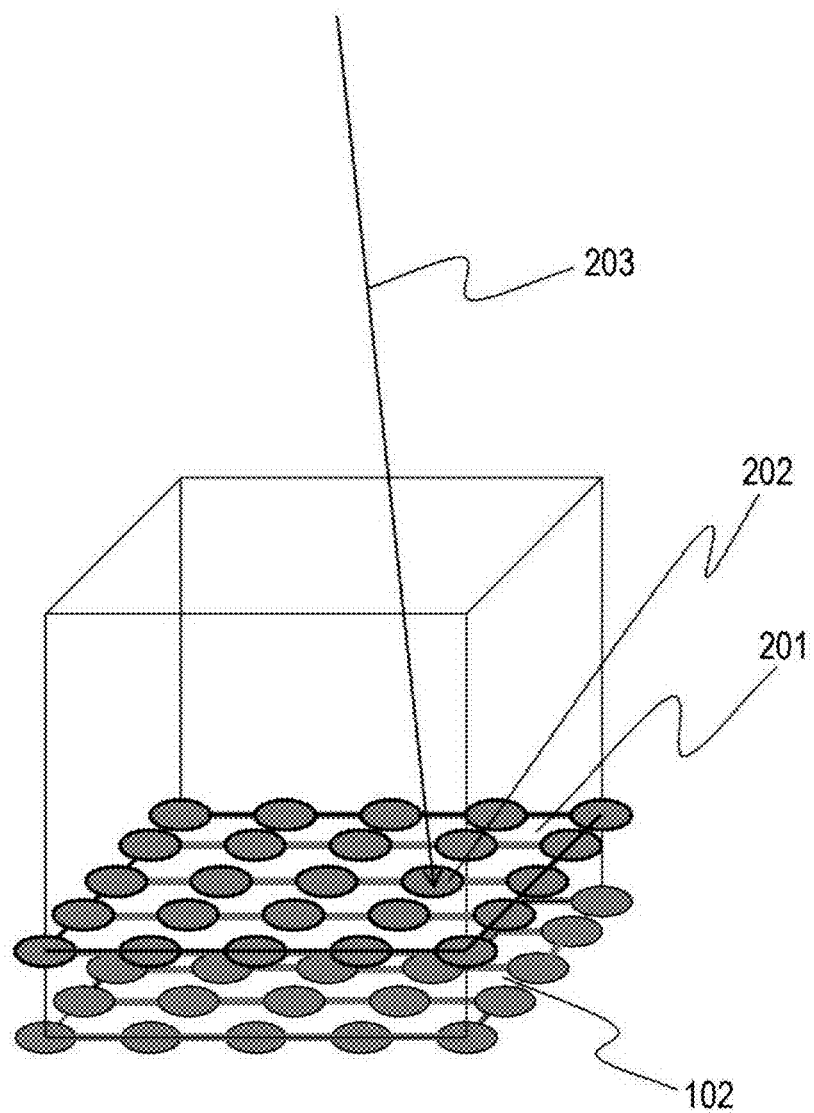
FIG. 4 is a perspective view illustrating a setting example of an irradiation position at the time of energy change in the raster scanning method.

FIG. 4 is a perspective view illustrating a setting example of an irradiation position at the time of energy change in the raster scanning method.

In the example of FIG. 4, a particle beam having energy lower than the energy used in FIG. 3 is extracted. Therefore, the particle beam stops at a position shallower than the plane 102 in FIG. 3. This stop position is represented by a plain 201 irradiated with the same energy. An irradiation spot 202 corresponding to the particle beam of this energy is irradiated with the particle beam passing through a trajectory 203 for irradiating the irradiation spot 202.

Another way to change the energy of the particle beam is to insert a range shifter (not shown) into the irradiation nozzle 400. The thickness of the range shifter is selected according to the energy to be changed. For the selection of the thickness, a method using a plurality of range shifters having a plurality of thicknesses or wedge-shaped range shifters facing each other may be used. Since the time required for the energy change in this method is only the time for inserting the range shifter, the energy change can be performed faster than the method for changing the setting of the synchrotron.

Figure 5:
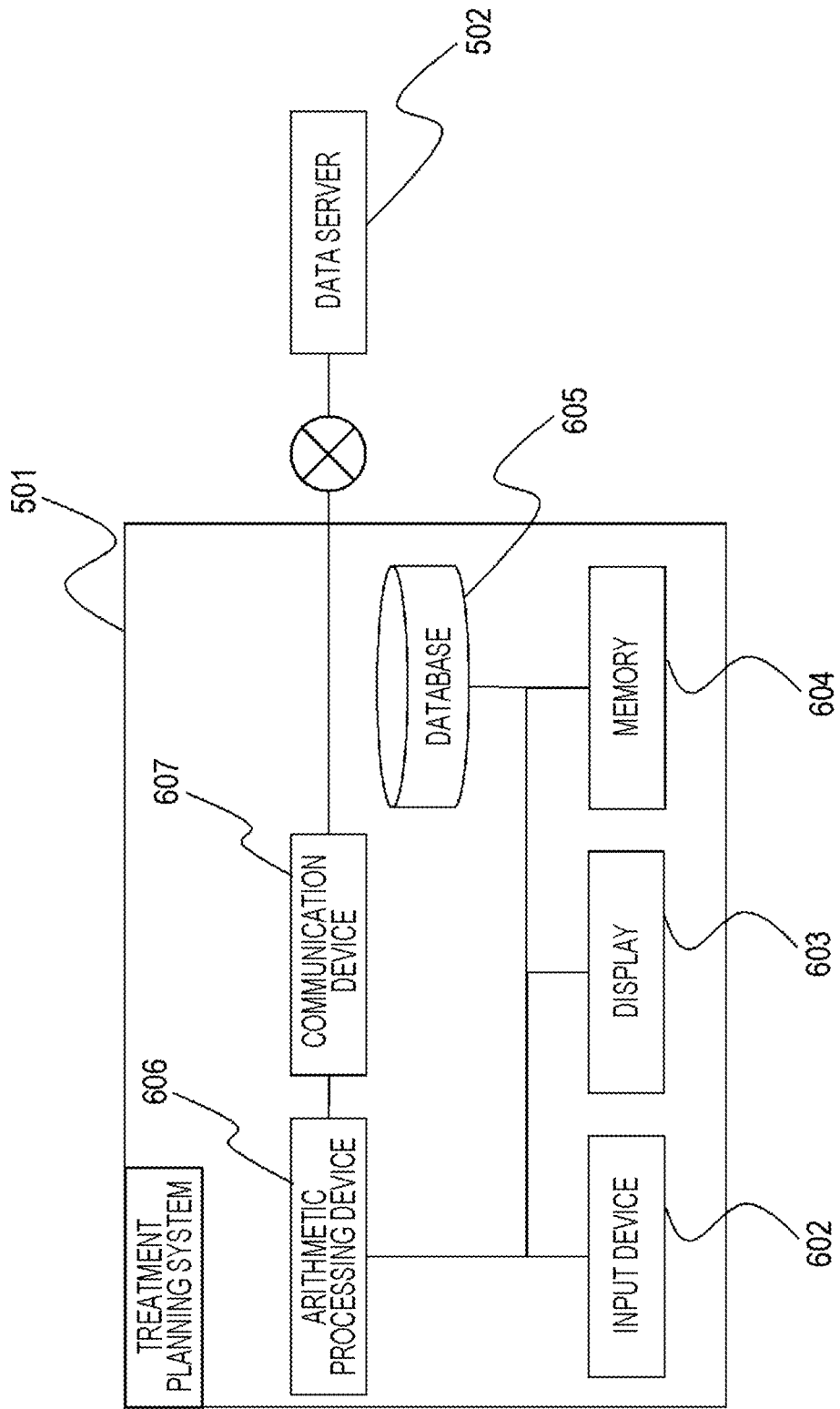
FIG. 5 is a diagram illustrating the treatment planning system according to the first embodiment.

FIG. 5 is a schematic configuration diagram illustrating the treatment planning system 501 according to first embodiment.

As illustrated in FIG. 5, the treatment planning system 501 includes an input device 602 for inputting a parameter for irradiating a particle beam, a display device 603 device for displaying treatment planning, a memory (storage medium) 604, a database (storage medium) 605, an arithmetic processing device 606 (control system as an arithmetic element) for performing dose distribution calculation, and a communication device 607. The arithmetic processing device 606 is connected to an input device 602, a display device 603, the memory 604, a database 605, and a communication device 607.

The treatment planning system 501 includes a device capable of performing various types of information processing, for example, an information processing device such as a computer. The information processing device includes an arithmetic element, a storage medium, and a communication interface which is the communication device 607, and further includes an input device 602 such as a mouse and a keyboard, and a display device 603 device such as a display.

The arithmetic element is, for example, a central processing unit (CPU), a graphic processing unit (GPU), a field-programmable gate array (FPGA), or the like. The storage medium includes, for example, a magnetic storage medium such as a hard disk drive (HDD), a semiconductor storage medium such as a random access memory (RAM), a read only memory (ROM), and a solid state drive (SSD), and the like. In addition, a combination of an optical disk such as a digital versatile disk (DVD) and an optical disk drive is also used as a storage medium. In addition, a known storage medium such as a magnetic tape medium is also used as the storage medium.

A program such as firmware is stored in the storage medium. At the start of the operation of the treatment planning system 501 (for example, at the time of turning on the power supply), a program such as firmware is read from this storage medium and executed to perform overall control of the treatment planning system 501. In addition to the program, the storage medium stores data and the like necessary for each processing of the treatment planning system 501.

Alternatively, some of the components constituting the treatment planning system 501 may be connected to each other via a local area network (LAN) or may be connected to each other via a wide area network (WAN) such as the Internet.

Next, the operation of the treatment planning system 501 of the present embodiment will be described with reference to FIGS. 6 to 8.

Figure 6:
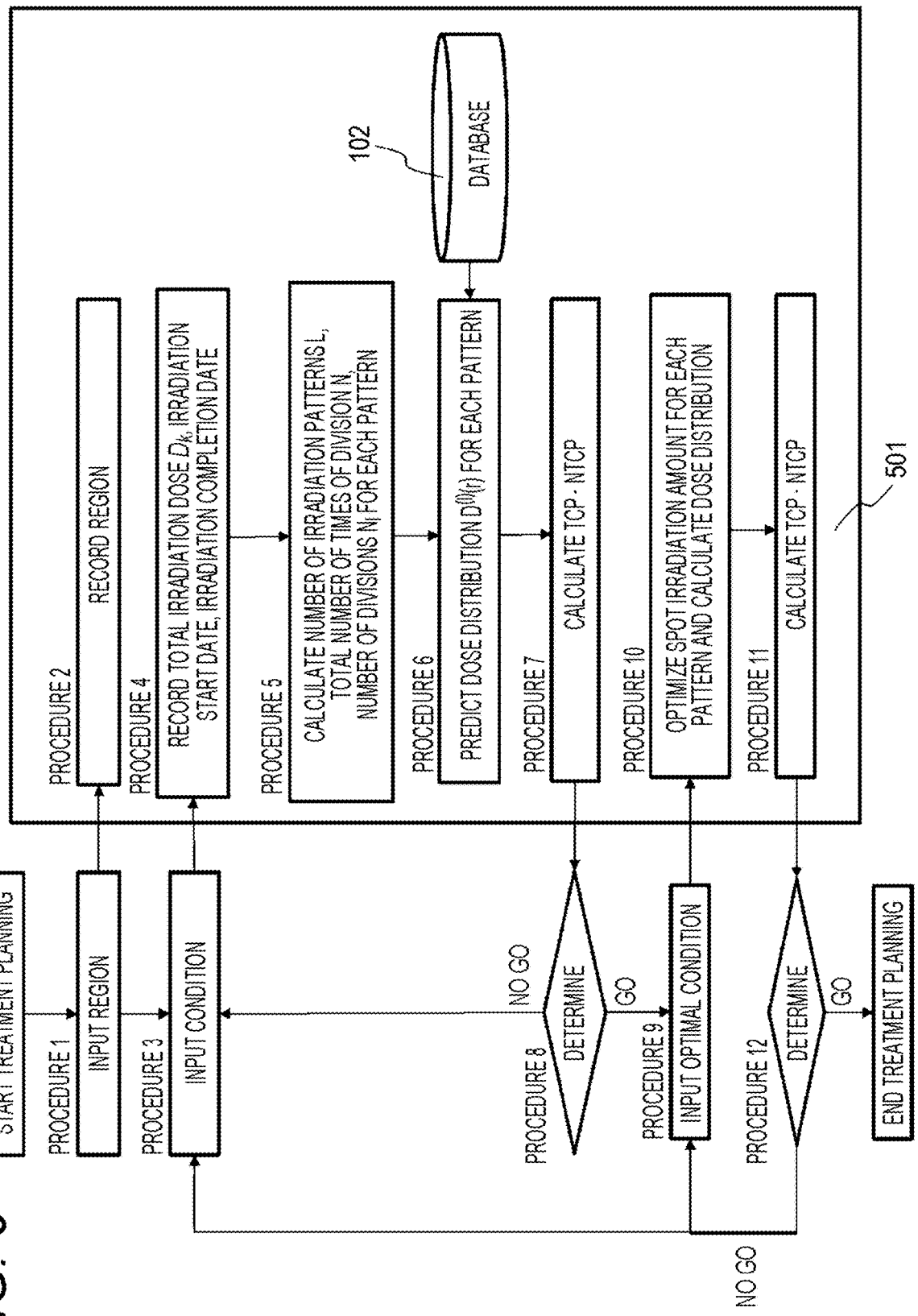
FIG. 6 is a flowchart illustrating a procedure for planning treatment planning by the treatment planning system according to the first embodiment.

FIG. 6 is a flowchart illustrating a procedure for planning treatment planning by the treatment planning system 501 according to the present embodiment.

As illustrated in FIG. 6, the operator first inputs a region to be designated for each slice of the CT image of an object to be irradiated using the input device 602 on the region input screen of the display device 603 (Procedure 1). That is, it is a target region to be irradiated with radiation and a region of an organ at risk (OAR) to be avoided from being irradiated with radiation as much as possible. When the input is completed in each slice, the region input by the operator is stored in the memory 604 as three-dimensional position information (Procedure 2).

Figure 7:
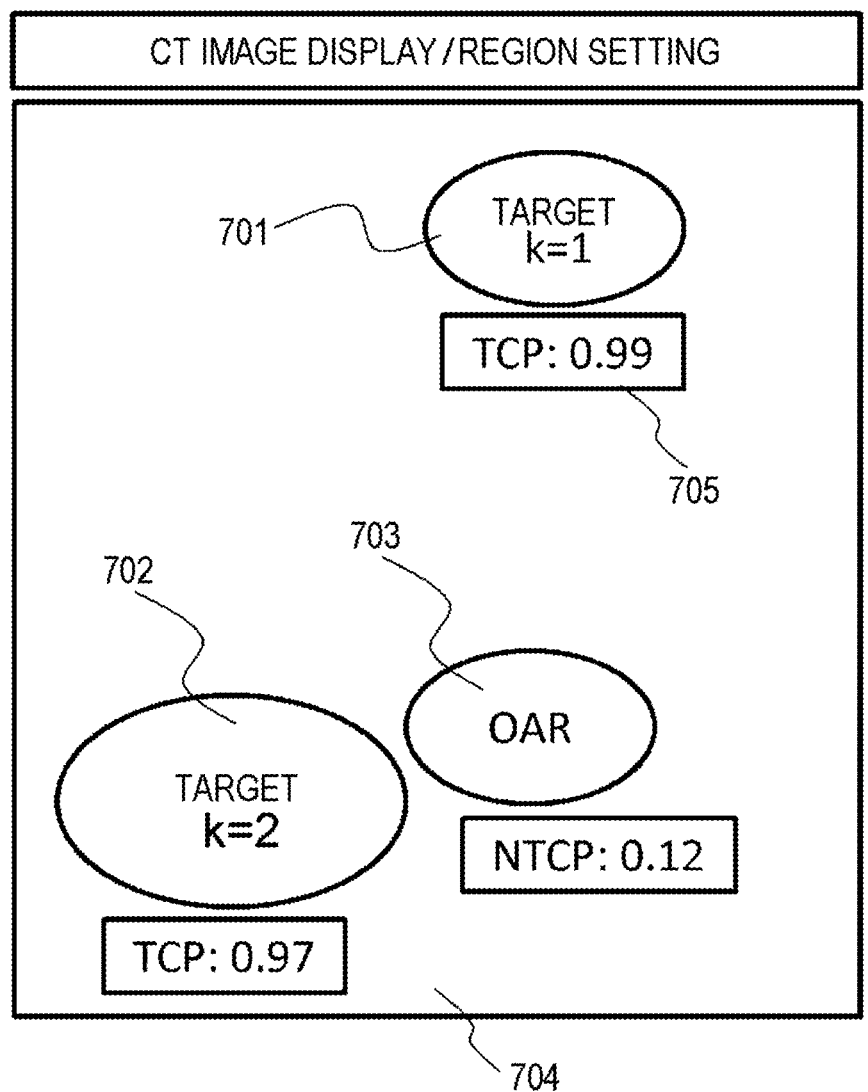
FIG. 7 is a schematic diagram of a GUI regarding a region input in the treatment planning system according to the first embodiment.

FIG. 7 illustrates, as an example, a state in which the operator inputs a target region 701 (target number k=1), a target region 702 (k=2), and an OAR 703 on a certain slice and draws the target regions on the GUI 704 on the display device 603.

Figure 8:
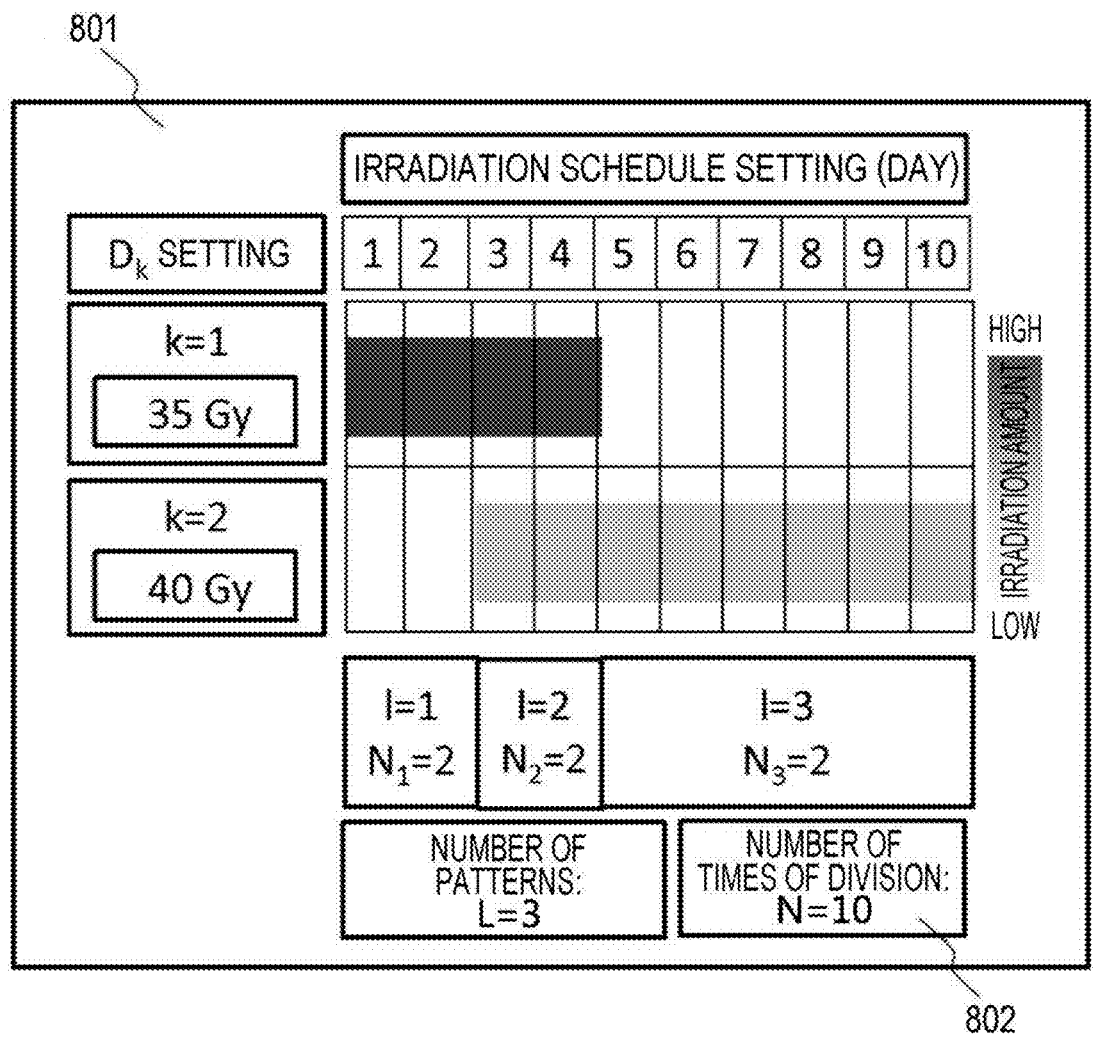
FIG. 8 is a schematic diagram of a GUI of a radiotherapy planning system regarding setting of an irradiation dose and treatment days for each target in the treatment planning system according to the first embodiment.

Further, the operator initially sets a total irradiation dose $D_k$, an irradiation start date, and an irradiation completion date for each target region k using the GUI 801 on the display device illustrated in FIG. 8 (Procedure 3). The set value is stored in a recording device (Procedure 4).

Next, the treatment planning system 501 calculates the number of irradiation patterns L necessary for treatment and the total number of times of division N of the entire treatment using the arithmetic processing device 606, and displays the results in the GUI 802 illustrated in FIG. 8 (Procedure 5). Specifically, the timing at which irradiation to the target is newly started and the timing at which irradiation to the target is completed are detected based on the irradiation start/completion date information for each target region k input to the GUI 301 illustrated in FIG. 8, and the switching timing of the irradiation pattern, the total number of irradiation patterns L, and the total number of times of division N of the entire treatment are calculated. Here, the irradiation pattern indicates a position of each spot and a prescribed irradiation dose to each spot.

Furthermore, in Procedure 5, the treatment planning system 501 calculates an irradiation dose $D^{(1)}_k$ to the target region k and the number of times of division $N_1$ in the first irradiation pattern based on the switching timing of the irradiation pattern, the total irradiation dose $D_k$ of each target region k, and the total number of times of division N of the entire treatment, and displays the results in a GUI 802 illustrated in FIG. 8. Here, Mathematical Formula 1 is satisfied.

$$D_k = \sum_1^L D_k^{(1)}, \quad N = \sum_1^L N_1.$$ [Mathematical Formula 1]

Next, the treatment planning system 501 predicts the dose distribution in the irradiation pattern 1 based on the past treatment results (Procedure 6). First, the arithmetic processing device 606 evenly arranges the point sequences $P_k^{(0)}(q)$ on the surface of the target region k. q is a number of a point sequence arranged on each target surface. Next, a normal vector $h_k(q)$ with respect to the target is calculated for each point, and an enlarged target region is calculated as a region surrounded by points $P_k^{(1)}(q)$ described below.

$$P_k^{(1)}(q) = h_k(q) + P_k^{(0)}(q)$$ [Mathematical Formula 2]

In the present embodiment, the size of $h_k(q)$ is 1 to 10 mm, and is constant regardless of k and q, but the same effect of the invention can be obtained even if the size is individually adjusted. This calculation is repeated to gradually expand the target. That is, the j-th enlarged target is a region surrounded by the following point sequence.

$$P_k^{(j)}(q) = h_k(q) + P_k^{(j-1)}(q)$$ [Mathematical Formula 3]

In the database 605, the average dose application rate $w_j$ in the difference region $dV_k^{(j)}$ between the enlarged target region surrounded by the point sequences $P_k^{(j)}(q)$ and the enlarged target region surrounded by the point sequences $P_k^{(j-1)}(q)$ is calculated from the past treatment results and recorded. In general, in radiotherapy, the dose attenuates as the distance from the target increases, and thus the dose application rate $w_j$ of $dV_k^{(j)}$ decreases as the target expansion progresses.

Next, the arithmetic processing device 606 provided in the treatment planning system 501 assumes that the dose $D^{(1)}_k$ is uniformly applied to the target k in the irradiation pattern 1, and calculates the dose $d_k^{(j)}$ applied to $dV_k^{(j)}$ as $w_j D^{(1)}_k$. Obviously, $w_0 = 1.0$ is satisfied. As a result, the dose $D^{(1)}(r)$ applied to an optional position r on the CT image in the irradiation pattern 1 is obtained by the following formula.

$$D^{(1)}(r) = \sum_k^K \sum_j^J d_k^{(j)} \begin{cases} r \subseteq dV_k^{(j)}: & d_k^{(j)} = w_j D_k^{(1)} \\ r \not\subseteq dV_k^{(j)}: & d_k^{(j)} = 0 \end{cases}$$ [Mathematical Formula 4]

Here, K represents the total number of target regions (in the present embodiment, K=2), and J represents the target expansion number. The target expansion number is set in advance in the treatment planning system 501 by the operator. In this manner, the dose applied to an optional position r in the irradiation pattern 1 is calculated with a small calculation amount without performing optimization.

In the present embodiment, a method for predicting $D^{(1)}(r)$ by adopting a model, in which the dose distribution $D^{(1)}(r)$ isotropically spreads about the target and attenuates as it goes away from the target and calculating the average dose at $dV_k^{(j)}$ from the past results of the treatment planning, was adopted. When the actual data is sufficiently accumulated, the same result as that of the present embodiment can be obtained by a method for estimating the dose distribution $D^{(1)}(r)$ using machine learning with the CT image and the three-dimensional position information of each region set in Procedure 1 and Procedure 2 as inputs.

Next, the treatment planning system 501 calculates a tumor control probability (TCP) and a normal tissue complication probability (NTCP) in the entire treatment based on the dose distribution $D^{(1)}(r)$ in the irradiation pattern 1 (Procedure 7). Considering the target region as a collection of micro volumes (hereinafter, referred to as Voxels), when a voxel i is irradiated with the dose $d_i$ once, a survival ratio of the tumor cells present in the voxel i is shown as follows. Here, i represents the voxel number.

$$\lambda_{d_i} = \exp\left\{-\alpha d_i \left(1 + \frac{\beta}{\alpha} d_i\right)\right\}$$ [Mathematical Formula 5]

Here, α and β are biological parameters determined by the type of target (for example, lung cancer, pancreatic cancer, and the like), and are measured by an experiment of irradiating cells with radiation or the like and set in the treatment planning system in advance by the operator. In a case of the treatment of the total number of times of division N, the total dose $D_i$, the following formula is satisfied.

$$\lambda_{D_i} = \lambda_{d_i} \times \lambda_{d_i} \times \lambda_{d_i} \cdots \times \lambda_{d_i} =$$ [Mathematical Formula 6]

$$\exp\left\{-\alpha D_i\left(1 + \frac{\beta}{N\alpha} D_i\right)\right\}$$

Therefore, in the treatment planning including L irradiation patterns as in the present embodiment, the calculation is performed as follows.

$$\lambda_{D_i} = \exp\left\{-\alpha D_i^{(l=1)}\left(1 + \frac{\beta}{\alpha}\frac{D_i^{(l=1)}}{N_{l=1}}\right) - \right.$$ [Mathematical Formula 7]

$$\left. \alpha D_i^{(l=2)}\left(1 + \frac{\beta}{\alpha}\frac{D_i^{(l=1)}}{N_{l=2}}\right) \ldots \right\} =$$

$$\exp\left\{\sum_l -\alpha D_i^{(l)}\left(1 + \frac{\beta}{\alpha}\frac{D_i^{(l)}}{N_L}\right)\right\}$$

It is known that the occurrence of cell death caused by radiation follows Poisson distribution. Assuming that the number of tumor cells included in each voxel of the target k before the start of the treatment is $n_k$, the number of tumor cells after the end of the treatment is calculated as $n_k \lambda_{Di}$ by Mathematical Formula 7, and thus the probability $P(\chi = 0)$ that the number of tumor cells $\chi$ in the voxel after the end of the treatment is zero can be expressed as follows.

$$P(\chi = 0) =$$ [Mathematical Formula 8]

$$\frac{\exp\{-n_k \lambda_{D_i}\}(n_k \lambda_{D_i})^\chi}{\chi!} = \exp\{-n_k \lambda_{D_i}\}$$

Since TCP is the probability that tumor cells will not survive in the target after the end of radiotherapy, by multiplying all the voxels included in the target k in Mathematical Formula 8, calculation is performed as follows.

$$TCP_k = \Pi_i \exp\{-n_k \lambda_{Di}\}$$ [Mathematical Formula 9]

The operator inputs $n_k$ to the treatment planning system in advance based on the test result and the past clinical data. As a matter of course, $n_k=0$ is satisfied for voxels not included in the target k.

The NTCP of the OAR is calculated by the following formula.

$$NTCP = \frac{1}{2}\left[1 - \mathrm{erf}\left(\frac{t}{\sqrt{2}}\right)\right] \quad \text{[Mathematical Formula 10]}$$

$$t = \frac{D_{max}V^{n_p} - TD_{50}}{m_p TD_{50}} \quad \text{[Mathematical Formula 11]}$$

$$D_{max}V^{n_p} = \sum_i \left\{(D'_i)^{\frac{1}{n_p}} \frac{V_i}{V}\right\}^{n_p} \quad \text{[Mathematical Formula 12]}$$

Here, $n_p$, $m_p$, and $TD_{50}$ are parameters determined for each OAR according to past clinical data and the like, and are input to the treatment planning system in advance by the operator. V is a volume of the OAR, and $v_i$ is a volume for each voxel when the OAR region is considered as a set of voxels as with the target. i indicates the number of the voxel included in the OAR. $D_i'$ is the converted total irradiation dose, and indicates the total irradiation dose at which the biological effect equivalent to that of the irradiation of the total irradiation dose $D_i$ and the total number of times of division N is obtained when the single irradiation dose $d_{ref}=2$ Gy.

When the total irradiation dose $D_i$ and the total number of times of division N, the probability that the normal tissue in the OAR survives is expressed as follows.

$$\lambda_{D_i} = \exp\left\{-\alpha D_i\left(1 + \frac{\beta}{\alpha}\frac{D_i}{N}\right)\right\} = \quad \text{[Mathematical Formula 13]}$$
$$\exp\left\{-\alpha N_{ref} d_{ref}\left(1 + \frac{\beta}{\alpha}d_{ref}\right)\right\}$$

Therefore, the converted total irradiation dose $D_i'=N_{ref}d_{ref}$ can be expressed as follows.

$$D'_i = D_i \frac{\alpha + \beta D_i/N}{\alpha + \beta d_{ref}} \quad \text{[Mathematical Formula 14]}$$

In the treatment planning including L irradiation patterns as in the present embodiment, the probability that the normal tissue in the OAR survives is expressed as follows.

$$\lambda_{D_i} = \exp\left\{\sum_l -\alpha D_i^{(l)}\left(1 + \frac{\beta}{\alpha}\frac{D_i^{(l)}}{N_j}\right)\right\} = \quad \text{[Mathematical Formula 15]}$$
$$\exp\left\{-\alpha N_{ref}d_{ref}\left(1 + \frac{\beta}{\alpha}d_{ref}\right)\right\}$$

Therefore, the converted total irradiation dose $D_i'$ is calculated by the treatment planning system 501 as follows.

$$D'_i = N_{ref}d_{ref} = \frac{\sum_l -\alpha D_i^{(l)}\left(1 + \frac{\beta}{\alpha}\frac{D_i^{(l)}}{N_j}\right)}{\frac{\alpha}{\beta} + d_{ref}} \quad \text{[Mathematical Formula 16]}$$

The TCP for each target and the NTCP for each OAR calculated based on the above formula are displayed in boxes 705 displayed in the vicinity of each region in the GUI 704 as illustrated in FIG. 7. The operator checks the displayed TCP/NTCP, and determines whether the treatment planning is good or bad (Procedure 8). When it is determined that improvement is necessary, the procedure returns to Procedure 3, the input parameters of the total irradiation dose $D_k$ to each target, the irradiation start date, and the irradiation completion date are corrected, and TCP/NTCP are calculated again.

In the present embodiment, in order to briefly describe the effects of the invention, the total irradiation dose $D_k$, the irradiation start date, and the irradiation completion date of each target, which are parameters of the treatment planning, are manually adjusted based on TCP/NTCP. However, a method for calculating a partial derivative or sensitivity matrix of TCP/NTCP for each parameter, and automatically updating and searching each parameter so as to maximize TCP and minimize NTCP can also obtain the same effects as the present invention.

When the calculated TCP/NTCP is determined to be appropriate, the operator determines the total irradiation dose $D_k$, the irradiation start date, and the irradiation completion date, and operates the treatment planning system 501 to optimize the beam irradiation dose for each spot in each irradiation pattern 1. First, the operator inputs a parameter necessary for optimization, for example, a weight (details will be described later) for each objective function (Procedure 9).

The treatment planning system 501 creates an objective function that quantifies a deviation between the dose distribution calculated based on the irradiation dose for each spot and the target value. Assuming that a vector having dose values at $M^{(k)}$ points set inside and around the target region k as an element is $d^{(k)}$, a relationship between $d^{(k)}$ and a vector x having a spot dose as an element can be expressed by the following formula.

$$d^{(k)}=Ax \quad \text{[Mathematical Formula 17]}$$

Here, a matrix A represents a dose (dose matrix) given to the calculation point in the target region from the beam with which each spot is irradiated, and is calculated on the basis of the irradiation direction set in advance by the operator or the in-vivo information by the CT image. Similarly, when a vector having dose values at $M^{(OAR)}$ points in the OAR as an element is $d^{(OAR)}$, it can be expressed as $d^{(OAR)}=Bx$. B represents a dose matrix similar to A.

The treatment planning system 501 sets a target irradiation dose $D^{(l)}_k/N_1$ for $M^{(k)}$ points corresponding to the target region. This corresponds to the daily irradiation dose to the target region k in the irradiation pattern 1. Furthermore, an allowable dose value $D^{(l)}_{lim}$ is set for $M^{(OAR)}$ points corresponding to the OAR. The allowable dose value $D^{(l)}_{lim}$ is input by the operator for each irradiation pattern 1. At this time, the treatment planning system 501 determines the objective function F(x) as in the following formula.

$$F(x) = \sum_k \sum_m^{M^{(k)}} w^{(k)}\left(d_m^{(k)} - \frac{D_k^{(1)}}{N_1}\right)^2 + \quad \text{[Mathematical Formula 18]}$$
$$\sum_m^{M^{(OAR)}} w^{(OAR)}\left(d_m^{(OAR)} - D_{lim}^{(1)}\right)^2 \theta\left(d_m^{(OAR)} - D_{lim}^{(1)}\right)$$

The first term is a portion corresponding to the target region, and the objective function F(x) decreases as the dose values at the $M^{(k)}$ points are closer to the prescription dose value $D^{(l)}_k/N_1$ set as the target. The second term is a term relating to the dose constraint of the OAR, and may be a dose that does not exceed the allowable dose $D^{(l)}_{lim}$. $\theta(d^{(OAR)}_m - D^{(l)}_{lim})$ is a staircase function, and is 0 when $d^{(OAR)}_m < D^{(l)}_{lim}$, and is 1 in other cases. Here, $w^{(k)}$ and $w^{(OAR)}$ are weights corresponding to the respective objective functions, and are values input by the operator. As the weight, a different numerical value can be set for each calculation point.

After generating the objective function F(x), the treatment planning system 501 searches for x having the smallest objective function F(x) by repeating iterative function until the end condition is satisfied. When the end condition is reached, the treatment planning system 501 ends the iterative function. As described above, indexes such as a calculation time, the number of calculations, and a change amount of an objective function are set as the end condition. The treatment planning system 501 calculates a dose distribution based on the spot dose finally obtained as a result of the iterative function, and displays the result on the display device 603. This procedure is performed for each irradiation pattern 1 (Procedure 10).

Next, based on the dose distribution calculated based on the optimized irradiation pattern 1, the treatment planning system 501 calculates TCP/NTCP for the entire treatment by the same algorithm as in Procedure 5 (Procedure 11). As in Procedure 5, the calculation result is displayed on the GUI 704 on the display device 603. The operator determines whether the planned treatment planning is good or bad based on the displayed calculation result, and completes the treatment planning when it is determined to be appropriate (Procedure 12). When it is determined that improvement is necessary, the procedure returns to Procedure 9, the weights $w^{(k)}$, $w^{(OAR)}$ of the objective function and the dose constraint value $D^{(l)}_{lim}$ for the OAR are adjusted, and the optimization of the irradiation pattern is repeated until an appropriate TCP/NTCP is obtained. Alternatively, returning to Procedure 3, the input parameters of the total irradiation dose $D_k$ to each target, the irradiation start date, and the irradiation completion date are corrected, and the optimization of the irradiation pattern is repeated until an appropriate TCP/NTCP is obtained.

Therefore, according to the treatment planning system 501 of the present embodiment, in treatment planning including a plurality of irradiation patterns, treatment planning based on an index for evaluating the validity of the irradiation pattern can be planned in a short time.

Second Embodiment

With reference to FIGS. 9 to 12, a radiotherapy planning system that enables planning of treatment planning in consideration of the influence of immunity, which is a second embodiment, will be described.

The radiotherapy planning system 501 described in the present embodiment assumes that relative biological effectiveness (RBE) of radiation changes every day due to immunity, and thus, optimizes the irradiation pattern in consideration of the daily change in the therapeutic effect due to immunity such that the maximum therapeutic effect can be obtained clinically.

Figure 9:
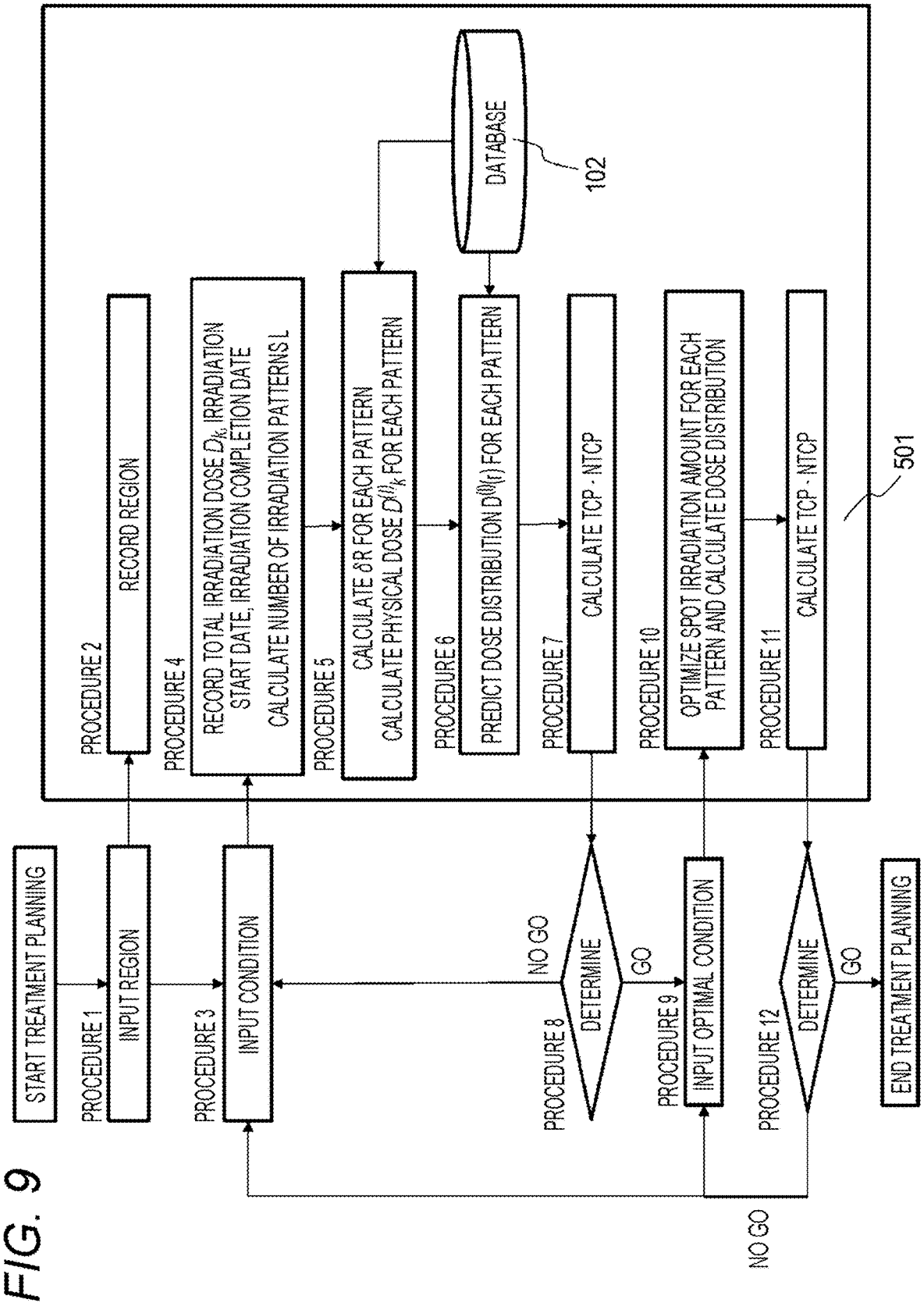
FIG. 9 is a flowchart illustrating a procedure for planning treatment planning in consideration of an immune effect by a treatment planning system according to the second embodiment.

As illustrated in the flowchart of FIG. 9, similarly to the first embodiment, the operator first inputs a region to be designated for each slice of the CT image of an object to be irradiated using the input device 602 on the region input screen of the display device 603 (Procedure 1). The region input by the operator is stored in the memory 604 of the treatment planning system 501 as three-dimensional position information (Procedure 2).

Figure 10:
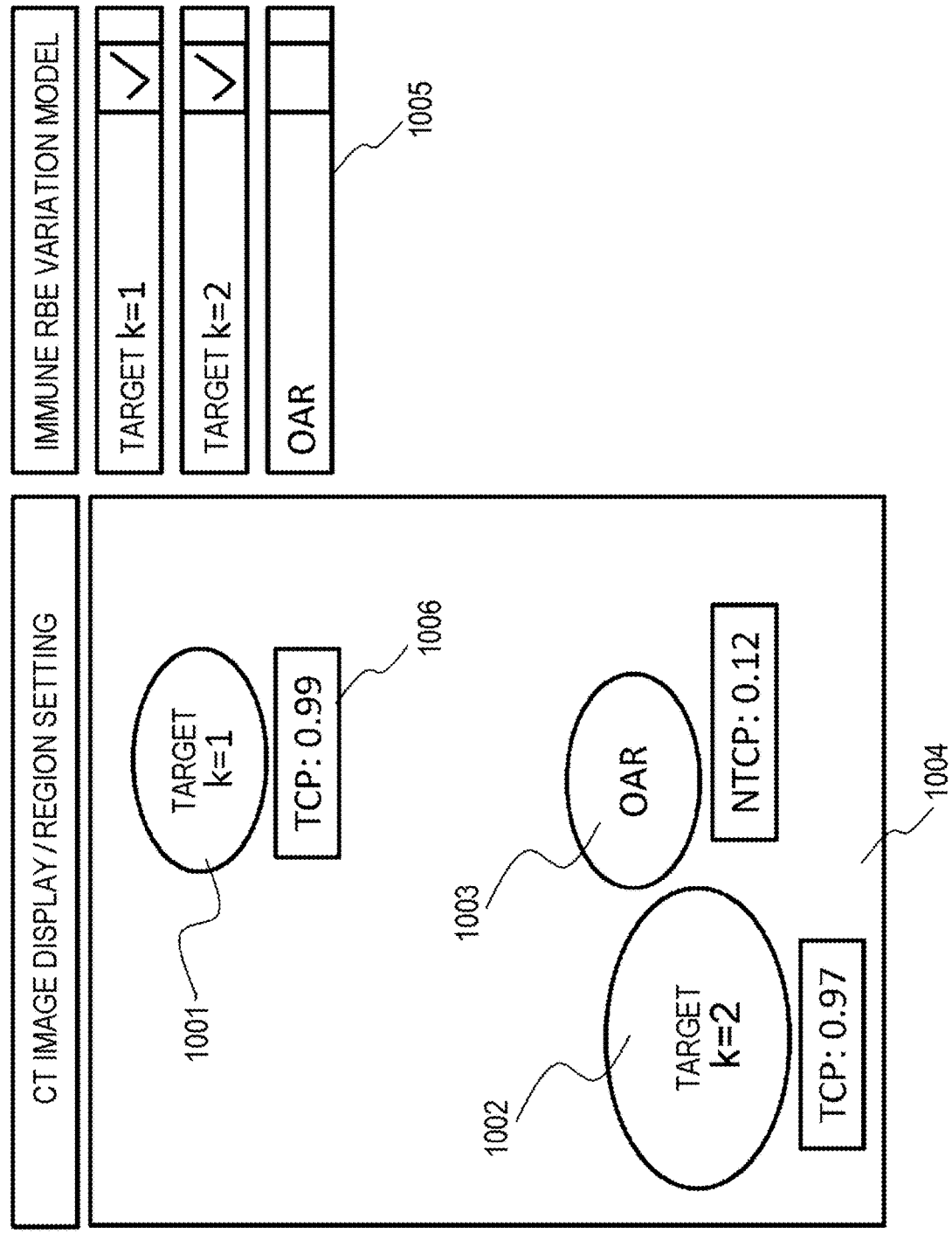
FIG. 10 is a schematic diagram of a GUI regarding a region input in the treatment planning system according to the second embodiment.

FIG. 10 illustrates, as an example, a state in which the operator inputs a target region 1001 (target number k=1), a target region 1002 (k=2), and an OAR 1003 on a certain slice and draws the target regions on the GUI 1004 on the display device 603. In the present embodiment, the target region 1002 (k=2) includes a lymph node. Furthermore, as illustrated in FIG. 10, the operator sets whether or not to consider variation in relative biological effectiveness (RBE) due to immunity for each region using a check box 1005.

Figure 11:
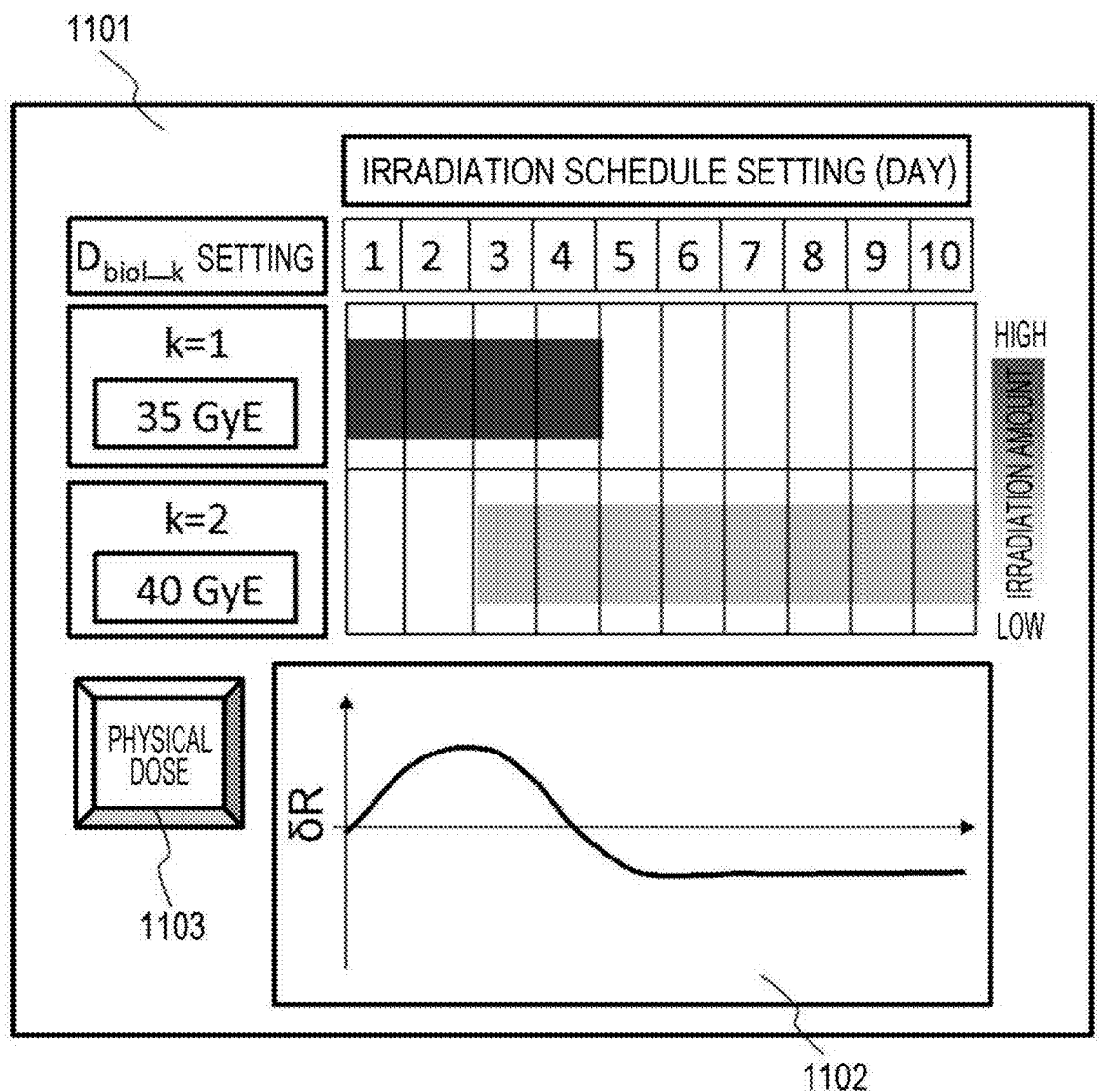
FIG. 11 is a schematic diagram of a GUI regarding setting of an irradiation dose and treatment days for each target in the treatment planning system according to the second embodiment.

Next, the operator initially sets the total biological irradiation dose $D_{biol\_k}$, the irradiation start date, and the irradiation completion date for each target region k from the GUI 1101 illustrated on the display device 603 illustrated in FIG. 11 (Procedure 3). The set value is stored in the memory 604 (Procedure 4). Further, in Procedure 4, the treatment planning system 501 calculates the number of irradiation patterns L required for treatment and the total number of times of division N of the entire treatment by the same method as in first embodiment. In second embodiment, L=N is satisfied. That is, the irradiation pattern is changed on all days.

Next, the treatment planning system 501 calculates the RBE variation $\delta R_1$ for each irradiation pattern 1, that is, for each day, with respect to the region set using the check box 1005 based on an immune RBE variation model stored in the database 605 (Procedure 5).

As illustrated in FIG. 11, the calculated $\delta R_1$ is displayed in a GUI 102 on the display device 603. In the example illustrated in FIG. 11, it is shown that the RBE is increased ($\delta R_1 > 1$) by irradiation of the target region 1001 (k=1), and then the RBE is decreased ($\delta R_1 < 1$) by irradiation of the target region 1002 (k=2) including the lymph node. In the region where the immune RBE variation model is not considered (in this embodiment, OAR 1003), $\delta R_1 = 1$ is satisfied.

The immune RBE variation model is created by past treatment results, cell irradiation experiments, and the like, and is registered in the treatment planning system in advance by the operator. In the present embodiment, the same immune RBE variation model is applied to the entire checked region, but different models can be used for each region.

Further, the treatment planning system 501 calculates the daily physical irradiation dose $D^{(l)}_k$ so as to keep the biological irradiation dose $D^{(l)}_{biol\_k}$ for each irradiation pattern 1 constant. That is, the calculation is performed as follows.

$$D^{(1)}_k = \frac{D^{(1)}_{biol\_k}}{RBE \times \delta R_1} \quad \text{[Mathematical Formula 19]}$$

Figure 12:
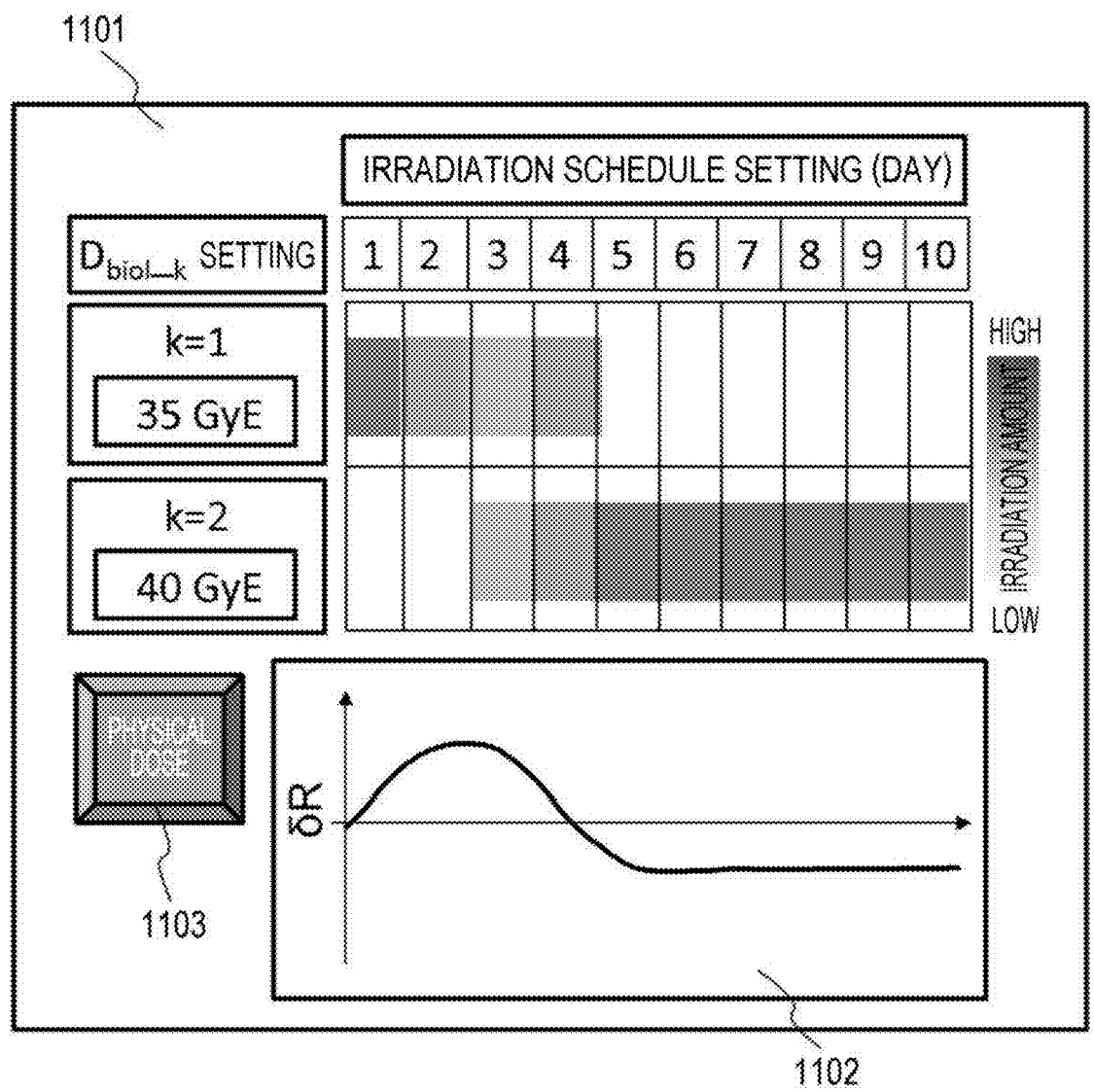
FIG. 12 illustrates a state in which a physical dose display button is activated in FIG. 11.

Here, RBE is a relative biological effectiveness of radiation determined by the quality of radiation. Since the present embodiment is proton beam therapy, the RBE is always 1.1. When the RBE is changed by linear energy transfer (LET) or the like as in a carbon ion beam, different RBE is applied to each voxel based on the residual range or the like of the beam. By pressing a switch button 1103, the calculated physical irradiation dose $D^{(l)}_k$ for each irradiation pattern 1 is shown on the display device 603. FIG. 12 is an image diagram of the GUI in a case where the switch button 1103 is activated in FIG. 11.

The following procedure is equivalent to first embodiment. First, the treatment planning system 501 predicts the dose distribution $D^{(I)}(r)$ in the irradiation pattern 1 based on the past treatment results (Procedure 6). Next, the treatment planning system calculates TCP and NTCP in the entire treatment based on the dose distribution $D^{(I)}(r)$ in the irradiation pattern 1 (Procedure 7). In second embodiment, since the irradiation pattern is changed every day, $N_1$ is always 1.

When the calculated TCP/NTCP is determined to be appropriate, the operator determines the total biological irradiation dose $D_{biol\_k}$, the irradiation start date, and the irradiation completion date. When it is determined that improvement is necessary, the procedure returns to Procedure 3, the input parameters of the total biological irradiation dose $D_{biol\_k}$ to each target, the irradiation start date, and the irradiation completion date are corrected, and TCP/NTCP are calculated again (Procedure 8).

Next, the operator inputs parameters (as described in the first embodiment, for example, it is a weight for each objective function) for optimizing the irradiation pattern to the treatment planning system 501 (Procedure 9). The treatment planning system optimizes the beam irradiation dose for each spot in each irradiation pattern 1 based on the input parameters and calculates a dose distribution (Procedure 10).

Next, based on the calculated dose distribution $D^{(I)}(r)$ of the entire irradiation pattern, the treatment planning system 501 calculates TCP/NTCP for the entire treatment by the same algorithm as in Procedure 7 (Procedure 11). The operator checks the calculation results of TCP/NTCP displayed on the display device, and determines whether the planned treatment planning is good or bad (Procedure 12). The treatment planning is completed if appropriate. When it is determined that improvement is necessary, the procedure returns to Procedure 9, the weights $w^{(k)}$, $w^{(OAR)}$ of the objective function and the dose constraint value $D^{(I)}_{lim}$ for the OAR are adjusted, and the optimization of the irradiation pattern is repeated until an appropriate TCP/NTCP is obtained. Alternatively, returning to Procedure 3, the input parameters of the total irradiation dose $D_{biol\_k}$ to each target, the irradiation start date, and the irradiation completion date are corrected, and the optimization of the irradiation pattern is repeated until an appropriate TCP/NTCP is obtained.

In addition, the present invention is not limited to the above-described embodiments, and includes various modifications. The above-described embodiments have been described in detail in order to describe the present invention in an easy-to-understand manner, and are not necessarily limited to those having all the described configurations. Further, a part of the configuration of one embodiment can be replaced with the configuration of another embodiment, and the configuration of another embodiment can be added to the configuration of one embodiment. Furthermore, it is possible to add, delete, and replace other configurations for a part of the configuration of each embodiment.

In addition, some or all of the above-described configurations, functions, processing units, processing means, and the like may be realized by hardware, for example, by designing with an integrated circuit. In addition, each of the above-described configurations, functions, and the like may be realized by software by a processor interpreting and executing a program for realizing each function. Information such as a program, a table, and a file for realizing each function can be stored in a recording device such as a memory, a hard disk, and an SSD, or a recording medium such as an IC card, an SD card, and a DVD.

In addition, control lines and information lines indicate what is considered necessary for explanation, and not all control lines and information lines are indicated on the product. In practice, it may be considered that almost all the configurations are connected to each other.

What is claimed is:

1. A treatment planning system that generates a treatment planning for irradiating a target with a particle beam, comprising:
   a control system that sets at least two or more irradiation patterns for one treatment planning, calculates a plurality of predicted dose distributions for each irradiation pattern of the at least two or more irradiation patterns based on a target dose set for each region for at least one region including a region of the target, and calculates an index for evaluating a validity of each irradiation pattern of the at least two or more irradiation patterns based on the plurality of predicted dose distributions.

2. The treatment planning system according to claim 1, further comprising:
   a database in which result data of the one treatment planning is recorded, wherein the control system calculates the plurality of predicted dose distributions based on the result data.

3. The treatment planning system according to claim 2, wherein the control system calculates the plurality of predicted dose distributions based on a prediction model that expands isotropically with respect to the target and gradually attenuates according to a distance from the target.

4. The treatment planning system according to claim 2,
   wherein a variation model of a relative biological effectiveness of radiation is recorded in the database, and
   wherein the control system calculates a physical irradiation dose such that a biological irradiation dose for each irradiation pattern of the at least two or more irradiation patterns is a constant based on the variation model for each region of the at least one region set to take into account a variation in the relative biological effectiveness of radiation.

5. The treatment planning system according to claim 1, wherein the index is at least one of a tumor control probability and a normal tissue complication probability.

6. The treatment planning system according to claim 5, wherein the control system calculates a gradient of the tumor control probability and the normal tissue complication probability with respect to a total irradiation dose, a treatment start date, and a treatment completion date set for each target, and updates the total irradiation dose, the treatment start date, and the treatment completion date in a direction in which the tumor control probability increases and the normal tissue complication probability decreases.

7. The treatment planning system according to claim 1, wherein the control system calculates the plurality of predicted dose distributions for each irradiation pattern of the at least two or more irradiation patterns also based on a number of divided doses set for each region of the at least one region.

8. The treatment planning system according to claim 7, further comprising:
   an input device that receives an input of setting values of the target dose and the number of divided doses, wherein the control system calculates the plurality of predicted dose distributions based on the target dose and the number of divided doses received in the input device.

9. The treatment planning system according to claim 1, wherein each irradiation pattern of the at least two or more irradiation patterns is an irradiation position of the particle beam set as the target and a prescribed irradiation dose of the particle beam for each irradiation position.

10. A treatment planning generation method by a treatment planning system that generates a treatment planning for irradiating a target with a particle beam, the treatment planning generation method comprising:
  setting at least two or more irradiation patterns for one treatment planning,
  calculating a plurality of predicted dose distributions for each irradiation pattern of the at least two or more irradiation patterns based on a target dose set for each region for at least one region including a region of the target, and
  calculating an index for evaluating a validity of each irradiation pattern of the at least two or more irradiation patterns based on the plurality of predicted dose distributions.

11. A non-transitory computer-readable recording medium containing a computer program executed by a computer that generates a treatment planning for irradiating a target with a particle beam, the computer program causing a computer to execute:
  a function of setting at least two or more irradiation patterns for one treatment planning,
  a function of calculating a plurality of predicted dose distributions for each irradiation pattern of the at least two or more irradiation patterns based on a target dose set for each region for at least one region including a region of the target, and
  a function of calculating an index for evaluating a validity of each irradiation pattern of the at least two or more irradiation patterns based on the plurality of predicted dose distributions.

* * * * *